United States Patent
Erkamp et al.

(10) Patent No.: US 10,888,352 B2
(45) Date of Patent: Jan. 12, 2021

(54) NEEDLE WITH PIEZOELECTRIC POLYMER SENSORS

(71) Applicant: KONINKLIJKE PHILIPS N.V., Eindhoven (NL)

(72) Inventors: Ramon Quido Erkamp, Swampscott, MA (US); Ameet Kumar Jain, Boston, MA (US); Francois Guy Gerard Marie Vignon, Croton on Hudson, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 511 days.

(21) Appl. No.: 15/301,579

(22) PCT Filed: Apr. 2, 2015

(86) PCT No.: PCT/IB2015/052425
§ 371 (c)(1),
(2) Date: Oct. 3, 2016

(87) PCT Pub. No.: WO2015/155645
PCT Pub. Date: Oct. 15, 2015

(65) Prior Publication Data
US 2017/0172618 A1 Jun. 22, 2017

Related U.S. Application Data

(60) Provisional application No. 61/978,193, filed on Apr. 10, 2014.

(51) Int. Cl.
*A61B 17/34* (2006.01)
*A61B 8/00* (2006.01)
(Continued)

(52) U.S. Cl.
CPC ........ *A61B 17/3403* (2013.01); *A61B 8/0841* (2013.01); *A61B 8/4494* (2013.01);
(Continued)

(58) Field of Classification Search
CPC . A61B 17/3403; A61B 17/3417; A61B 90/39; A61B 8/4494; A61B 8/0841;
(Continued)

(56) References Cited

U.S. PATENT DOCUMENTS 4,517,665 A * 5/1985 DeReggi ............... B06B 1/0688
310/800
6,217,518 B1 * 4/2001 Holdaway ............ A61B 5/6848
600/439

(Continued)

FOREIGN PATENT DOCUMENTS

JP  11206759 A  8/1999
JP  2013034665 A  2/2013
(Continued)

OTHER PUBLICATIONS

Barr, Richard G. "Improved Needle Visualization with Electronic Beam Steering", Ultrasound Quarterly, vol. 28, No. 2, Jun. 2012.
(Continued)

*Primary Examiner* — Theodore J Stigell
*Assistant Examiner* — Johnathan Maynard (57) ABSTRACT

A medical device includes a conductive body having a surface and a sensor conformally formed on the surface and including a piezoelectric polymer formed about a portion of the surface and following a contour of the surface. The piezoelectric polymer is configured to generate or receive ultrasonic energy. Electrical connections conform to the surface and are connected to an electrode in contact with the piezoelectric polymer. The electrical connections provide connections to the piezo electric polymer and are electrically
(Continued)

isolated from the conductive body over a portion of the surface.

20 Claims, 7 Drawing Sheets (51) Int. Cl.
    *A61B 8/08*     (2006.01)
    *A61B 90/00*     (2016.01)
    *A61B 34/20*     (2016.01)
    *A61B 18/14*     (2006.01)
    *A61B 18/00*     (2006.01)

(52) U.S. Cl.
    CPC .......... *A61B 17/3417* (2013.01); *A61B 90/39* (2016.02); *A61B 2017/3413* (2013.01); *A61B 2018/0088* (2013.01); *A61B 2018/00345* (2013.01); *A61B 2018/00529* (2013.01); *A61B 2018/1425* (2013.01); *A61B 2034/2063* (2016.02); *A61B 2090/3925* (2016.02); *A61B 2090/3929* (2016.02)

(58) Field of Classification Search
    CPC ........... A61B 2018/00345; A61B 2018/00529; A61B 2018/0088; A61B 2090/3929; A61B 2090/3925; A61B 2018/1425; A61B 2034/2063; A61B 2017/3413; A61B 8/12
    See application file for complete search history.

(56) References Cited

U.S. PATENT DOCUMENTS

| | | |
|---|---|---|
| 2001/0047134 A1 | 11/2001 | Holdaway |
| 2007/0164632 A1 | 7/2007 | Adachi |
| 2012/0059260 A1 | 3/2012 | Robinson |
| 2013/0018269 A1 | 1/2013 | Hasegawa |

FOREIGN PATENT DOCUMENTS

| | | |
|---|---|---|
| RU | 2380121 C1 | 1/2010 |
| WO | 199808440 A1 | 3/1998 |
| WO | 2007123444 A1 | 11/2007 |

OTHER PUBLICATIONS

Nichols, Kremer et al "Changes in Ultrasonographic Echogenicity and Visibility of Needles with Changes in Angles of Insonation", J Vasc Interv Radiology, vol. 14, No. 12, 2003.

Cheung, Stphanic et al "Enhancement of needle visibility in ultrasound-guided percutaneous procedures", Ultrasound in Medicine & Biology, vol. 30, Issue 5, May 2004—Abstract Only.

* cited by examiner

NEEDLE WITH PIEZOELECTRIC POLYMER SENSORS

CROSS-REFERENCE TO PRIOR APPLICATIONS

This application is the U.S. National Phase application under 35 U.S.C. § 371 of International Application No. PCT/IB2015/052425, filed on Apr. 2, 2015, which claims the benefit of U.S. Provisional Patent Application No. 61/978,193, filed on Apr. 10, 2014. These applications are hereby incorporated by reference herein.

BACKGROUND

Technical Field

This disclosure relates to medical instruments and more particularly to a system and method to track a tip of a needle or other devices under ultrasound guidance using ultrasound receivers formed on the needle.

Description of the Related Art

In ultrasound imaging, the visibility of the needle is often very poor due to the specular nature of the needle surface that reflects beams away from the imaging probe. To alleviate this problem some needle manufacturers have produced needles with special echogenic coatings, but the visualization improvement is limited. Ultrasound imaging system manufacturers have developed algorithms that use multiple imaging beams from varied angles, but improvement is limited and such a strategy is primarily suited only for linear arrays. Both strategies do not help when the needle is inserted perpendicular to the imaging plane or the needle path has a small offset relative to the imaging plane.

One solution that has been proposed to visualize the tip of interventional tools such as needles, but also catheters, is to add ultrasound receivers near the tip of the tool. While the imaging beam sweeps the field of view, the signals from the sensors indicate how close the beams are getting to the sensor. This information is used to calculate sensor position relative to the ultrasound image with positional accuracy exceeding 0.5 mm, even under conditions where the needle is not visible in the ultrasound image. The sensor needs to not interfere with the functionality of the device (e.g., not block the lumen, not interfere with the mechanics, e.g., for an automatic biopsy device, etc.).

SUMMARY

In accordance with the present principles, a medical device includes a conductive body including a surface. A sensor is conformally formed on the surface and includes a piezoelectric polymer formed about a portion of the surface and following a contour of the surface. The piezoelectric polymer is configured to generate or receive ultrasonic energy. Electrical connections conform to the surface and are connected to an electrode in contact with the piezoelectric polymer. The electrical connections provide connections to the piezoelectric polymer and are electrically isolated from the conductive body over the surface.

Another medical device includes a conductive body having a surface and a sensor conformally formed on the surface. The sensor includes a piezoelectric polymer formed about a portion of the surface and following a contour of the surface and an electrode formed over the piezoelectric polymer and including a trace connecting to the electrode and extending along the conductive body proximally to the electrode. A first dielectric layer is formed over the conductive body adjacent to the piezoelectric polymer and extends proximally to the piezoelectric polymer. A second dielectric layer is formed adjacent to the electrode over the trace and extends proximally to the electrode. A conductive shield is formed over the second dielectric layer.

A method for fabricating a medical device includes conformally forming a sensor on a conductive body including a surface by: applying a piezoelectric polymer about a portion of the surface that follows a contour of the surface; forming a first dielectric layer over the conductive body adjacent to the piezoelectric polymer and extending proximally to the piezoelectric polymer; forming an electrode over the piezoelectric polymer including a trace connecting to the electrode and extending along the first dielectric layer proximally to the electrode; forming a second dielectric layer adjacent to the electrode over the trace and extending proximally to the electrode; forming a conductive shield formed over the second dielectric layer; and forming an outer dielectric layer over the conductive shield and the electrode.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, systems, devices and methods are provided for tracking a needle (or other device) under ultrasound guidance by attaching small ultrasound receivers onto the device. The present principles provide a needle, device or system that includes one or more low profile sensors at very low per device cost and permits scaling for mass production to maintain low cost.

The ultrasound sensors may be formed on the needle or other device and may be fabricated using a piezoelectric polymer, e.g., polyvinylidene fluoride (PVDF) or polyvinylidene fluoride trifluoroethylene (P(VDF-TrFE)). P(VDF-TrFE), which can be dissolved in acetone and applied to the needle through an evaporative process. The sensors are high impedance and can be modeled as a voltage source in series with a small capacitor (e.g., 2.2 pF). Such a sensor is very sensitive to capacitive loading of the electrical interconnect, and special capacitance cancelling electronics (similar to, e.g., a driven shield technique) can be employed to avoid large signal loss. A wire carrying the signal preferably is shielded (e.g., includes an electric shield around the conductor). This may be accomplished using a stripline configuration.

It should be understood that the present invention will be described in terms of medical instruments; however, the teachings of the present invention are much broader and are applicable to any instrument that can accept a low profile sensor. In some embodiments, the present principles are employed in tracking or analyzing complex biological or mechanical systems. In particular, the present principles are applicable to internal tracking procedures of biological systems and are applicable for procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Referring now to the drawings in which like numerals represent the same or similar elements and initially to FIGS. 1A-1F, perspective views showing the fabricating of a single ring sensor 10 on a tip 12 of a needle 14 are illustratively shown in accordance with one embodiment.

Figure 1A:
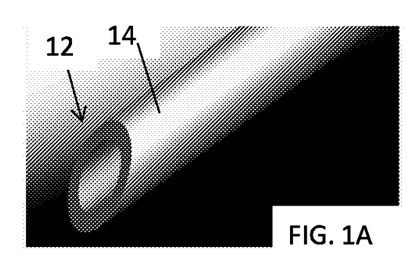
FIG. 1A is a perspective view showing a needle where a low profile conformal sensor will be formed in accordance with the present principles.

Referring to FIG. 1A, the needle 14 is depicted prior to the formation of sensor 10. The needle 14 preferably includes a metal, such as a stainless steel although other surgically compatible materials may be employed.

Figure 1B:
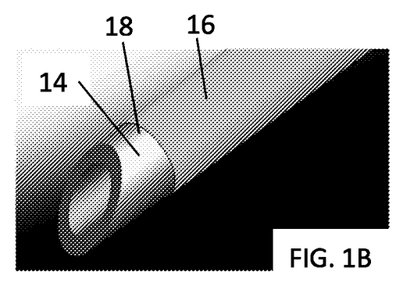
FIG. 1B is a perspective view showing the needle of FIG. 1A having a dielectric layer (insulator) formed thereon in accordance with the present principles.

Referring to FIG. 1B, an insulator 16 is deposited or printed on the needle 14. The insulator 16 may include any suitable dielectric material that adheres to the needle 14. The insulator 16 may be about 25-50 microns thick although other thicknesses may be employed. The insulator 16 is deposited on the needle 14 without covering a small section at the tip region. This may be accomplished in a plurality of ways. For example, the portion may be masked and etched away or the needle may be dip coated from the proximal end of the needle 14.

Figure 1C:
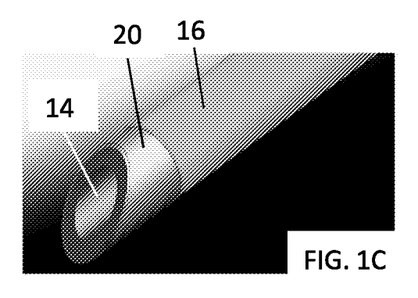
FIG. 1C is a perspective view showing the needle of FIG. 1B having a copolymer (piezoelectric polymer) formed thereon in accordance with the present principles.

Referring to FIG. 1C, the tip portion (distal end portion) of the needle 14 is coated with a piezoelectric copolymer 20. This may be achieved by employing a dip coating process. Special care needs to be taken that the copolymer 20 touches or slightly overlaps the insulator layer 16 such that the needle surface is not exposed in a small section (18, FIG. 1B). The metal needle 14 now serves as a bottom electrode for the copolymer sensor 10. In one embodiment, the copolymer includes a P(VDF-TrFE) ring, although other suitable materials may be employed.

Figure 1D:
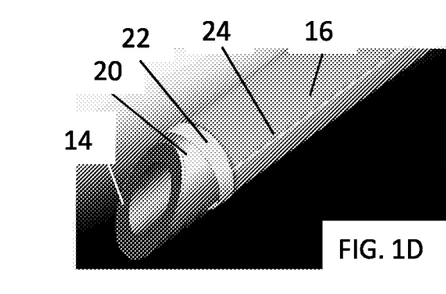
FIG. 1D is a perspective view showing the needle of FIG. 1C having a top electrode formed on the copolymer and a trace formed on the dielectric layer in accordance with the present principles.

Referring to FIG. 1D, a top electrode 22 and a signal trace 24 connecting to the top electrode 22 are applied. The top electrode 22 may be formed over the copolymer 20 at the distal end portion, and the trace 24 may be formed over the insulator 16 toward the proximal end portion of the needle 14. The proximal end portion of the trace 24 will connect to a hub side contact (not shown). The top electrode 22 and the trace 24 may be printed using a conductive ink. Other processes may be employed as well such as, e.g., masked vapor deposition or vapor deposition and etching. The material for top electrode 22 and trace 24 may also include deposited metals such as silver, gold, etc. The top electrode 22 and the trace 24 may have a thickness of less than one micron to a few microns.

Figure 1E:
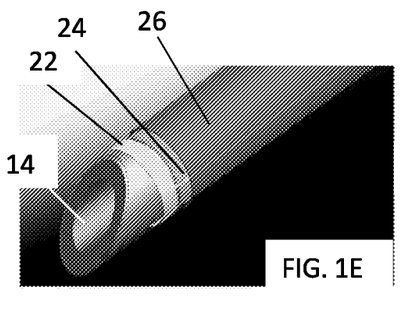
FIG. 1E is a perspective view showing the needle of FIG. 1D having another dielectric layer (insulator) formed on the trace in accordance with the present principles.

Referring to FIG. 1E, another insulator 26 is formed over the trace 24 and insulator layer 16. This insulator 26 may be produced by dip coating from the proximal end portion of the needle 14. The insulator 26 is deposited or printed on the needle 14. The insulator 26 may include any suitable dielectric material that adheres to underlying materials. The insulator 26 may be about 25-50 microns thick although other thicknesses may be employed.

Figure 1F:
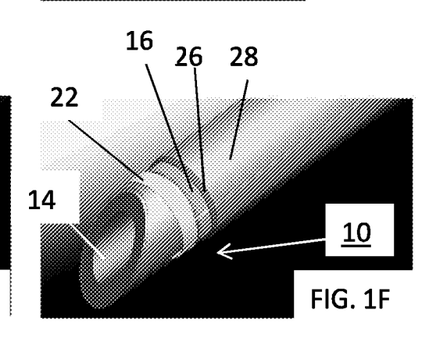
FIG. 1F is a perspective view showing the needle of FIG. 1E having a conductive shield formed thereon in accordance with the present principles.

Referring to FIG. 1F, a conductive shield 28 is applied over the insulator 26. The conductive shield 28 may be produced by vapor deposition or dip coating in conductive ink. Care needs to be taken to not cover the tip (distal end portion of the needle 14). The needle 14 and outer shield 28 will be coupled together as they form a driven shield. To electrically insulate the top electrode 22 from the surroundings and ensure biocompatibility, the whole needle could be covered with, for example, parylene or other outer dielectric material (not shown). If the parylene coating (outer dielectric) is extremely thin, there may be a capacitive coupling from the top electrode 22 to a body (where the needle 14 will be inserted) and the body to the outer shield 28. With a conductive body, this could create a shunt path across the sensor 10 and thus form a low pass filter. Care needs to be taken that the cut off frequency is significantly above the ultrasound frequency of interest. Alternatively, the outer dielectric and outer shield 28 could be made to go over the tip, thereby insulating the top electrode 22 (but possibly slightly degrade sensitivity as the acoustic wave has to pass through it). By properly selecting acoustic properties and thicknesses, the outer dielectric may serve as an acoustic matching layer.

For the dielectric layers, e.g., insulator 16, 26 and the outer dielectric, it is advantageous to select a material with a relatively low dielectric constant. For example, polytetrafluoroethylene (PTFE) with a dielectric constant of about 2.1 may be selected. However, the adhesion of PTFE to other materials may be an issue. Other materials, such as biocompatible polypropylene (dielectric constant 2.2) may be employed. Many plastics/polymers have a dielectric constant close to 3.0 and may also be employed. Polyurethane has a slightly higher 3.5 value and is attractive for use in the present applications because there are medical grade versions (used to coat implantable pacemakers). Further, polyurethane provides good adhesion to many materials with high smoothness and durability, and can be deposited in thin layers using appropriate solvents. Other materials may also be used.

The single ring sensor 10 provides maximum sensor sensitivity due to a strong impedance difference between the conductor (22) of the sensor 10 and its backing material (20). The narrow trace 24 is provided that minimizes the capacitive loading of the sensor 10. The thin interconnect trace 24 is shielded similarly to a stripline configuration to be optimized for low capacitance. The sensor 10 can be more sensitive to injected noise as the needle 14, that is in electrical contact with tissue (when filled with fluid or stylet), is part of the interconnect.

The sensor 10 may include a P(VDF-TrFE) copolymer ring 20 shaped onto the needle 14. A ring contact pad structure (hub side contact) of the top electrode 22 is formed at a hub end portion (proximal end portion) and provides for low disposable cost connectivity. Specialized electronics can be provided to reduce signal loss due to capacitive loading of the interconnect. It should be understood that the sensors are integrally formed with the needle (or device) and as such the needle and the sensors are a disposable item.

The present principles can be extended to multiple sensors on a same needle. This permits a determination of orientation of the needle and also determination of the location of the needle tip without the need to place the sensor very close to the tip. Calculating the tip location based on signals from multiple sensors should also increase the measurement accuracy as well as provide an indication of confidence in the measurement. The cost is a slightly more complicated manufacturing process and a slight loss of signal because of the extra capacitive load of multiple sensors.

Figure 2A:
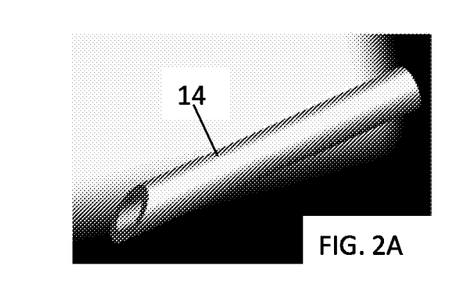
FIG. 2A is a perspective view showing a needle where dual low profile conformal sensors will be formed in accordance with the present principles.

Referring to FIGS. 2A-2F, a dual ring sensor embodiment includes multiple sensors formed on a needle or other device as illustratively shown. Two sensors will be formed along the needle 14 (FIG. 2A).

Figure 2B:
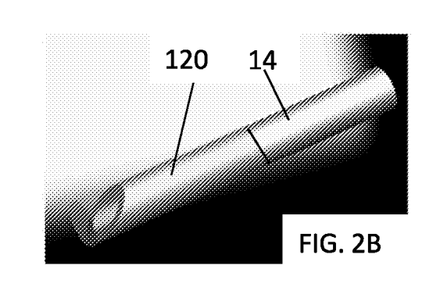
FIG. 2B is a perspective view showing the needle of FIG. 2A having a copolymer (piezoelectric polymer) formed on a distal end portion in accordance with the present principles.

Referring to FIG. 2B, the needle 14 is dip coated with a copolymer 120 that covers a whole range of sensor positions on the needle 14.

Figure 2C:
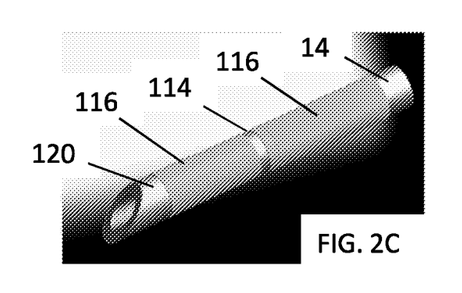
FIG. 2C is a perspective view showing the needle of FIG. 2B having a sectioned dielectric layer (insulator) formed thereon in accordance with the present principles.

Referring to FIG. 2C, a dielectric (insulator layer) 116 is applied, but needs to have a gap 114 where a second sensor ring is to be formed. This gap 114 can be created by applying a thin adhesive strip prior to dielectric deposition, then pulling off the strip to remove material and create the gap 114. Alternatively, the dielectric could be etched or scratched to create that gap 114. The dielectric 116 may be about 25-50 microns in thickness although other thicknesses may be employed. The gap 114 in the dielectric layer 116 (between sections) exposes the underlying polymer 120.

Figure 2D:
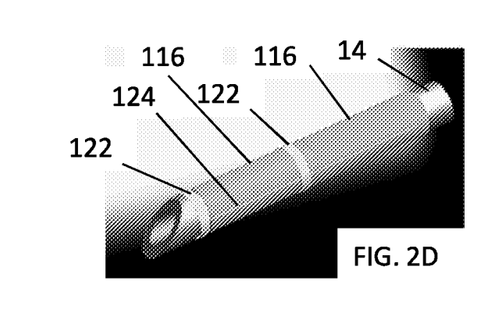
FIG. 2D is a perspective view showing the needle of FIG. 2C having top electrodes formed on the copolymer and traces formed on the dielectric layer for each electrode in accordance with the present principles.

Referring to FIG. 2D, two ring electrodes 122 and signal trace(s) 124 are deposited. The electrodes 122 and traces 124 may be sub-micron thicknesses. The ring electrodes 122 are formed on the polymer 120. Traces 124 may be formed at different locations about the needle 14. The traces 124 may connect the ring electrodes 122, or two traces 124 may be individually connected to the ring electrodes 122.

Figure 2E:
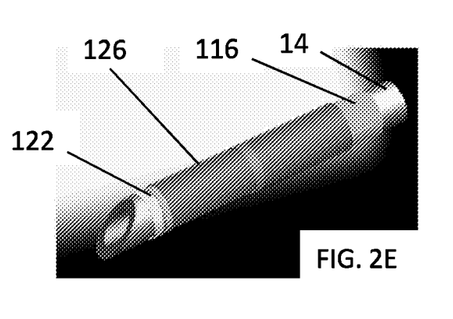
FIG. 2E is a perspective view showing the needle of FIG. 2D having another dielectric layer (insulator) formed on the traces in accordance with the present principles.

Referring to FIG. 2E, another insulator 126 is formed over the proximal portion of the top electrode 122 and over the trace 124. The insulator 126 may be about 25-50 microns thick although other thicknesses may be employed.

Figure 2F:
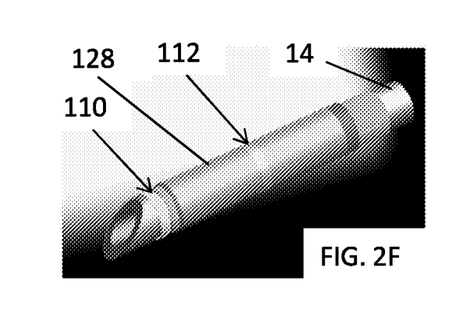
FIG. 2F is a perspective view showing the needle of FIG. 2E having a conductive shield formed thereon in accordance with the present principles.

Referring to FIG. 2F, a conductive shield 128 is applied over the insulator 126. The conductive shield 128 may be produced by vapor deposition or dip coating in conductive ink. Care needs to be taken to not cover the tip (distal end portion of the needle 14). The needle 14 and outer shield 128 will be connected together as they form a driven shield. To electrically insulate the top electrode 122 from the surroundings and ensure biocompatibility, the whole needle could be covered with an outer dielectric material (not shown).

The two sensors 110 and 112 are electrically connected in parallel (one trace 124 connecting both sensors 110 and 112) and knowledge of the ultrasonic emission sequence needs to be used to determine which of the sensors 110, 112 is receiving a signal. There is also a slight signal loss because the sensor rings are electrically loading each other. It is possible to bring out separate signal traces for each sensor, but this may complicate the manufacturing process.

The embodiments of FIGS. 1A-F and FIGS. 2A-F have the copolymer sensor placed in direct electrical contact with the needle. As the needle is in direct contact with bodily fluids there is a possibility that electrical noise is injected into an amplifier coupled to the sensors. In accordance with other embodiments, an insulated single ring sensor is provided.

This design protects against outside signals interfering with measurements, at the cost of some sensitivity and a more complex manufacturing method. It should be understood that the sensors are integrally formed with the needle (or device) and as such the needle and the sensors are a disposable item.

Figure 3A:
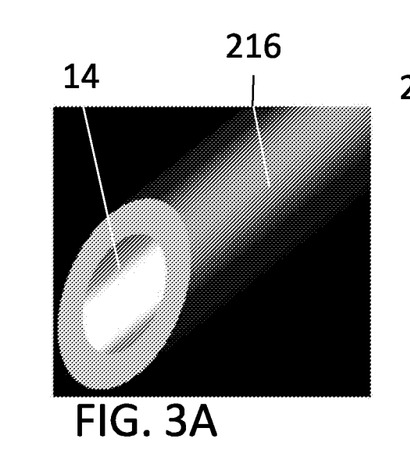
FIG. 3A is a perspective view showing a needle where a low profile conformal sensor will be formed, coated with a dielectric layer in accordance with another embodiment.
Figure 3B:
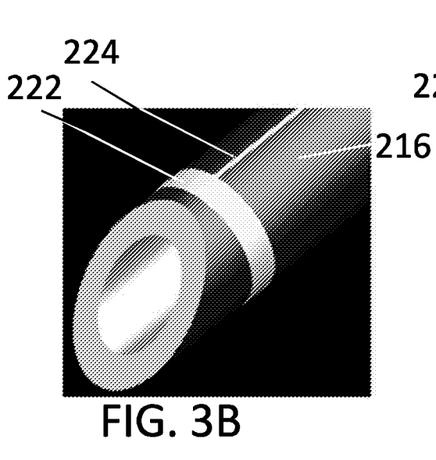
FIG. 3B is a perspective view showing the needle of FIG. 3A having an electrode and trace formed on the dielectric layer in accordance with the present principles.
Figure 3C:
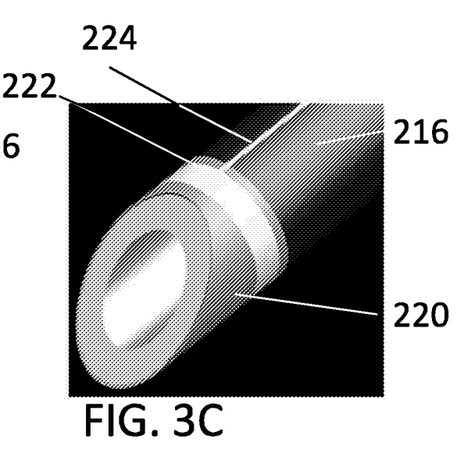
FIG. 3C is a perspective view showing the needle of FIG. 3B having a copolymer (piezoelectric polymer) formed thereon in accordance with the present principles.
Figure 3D:
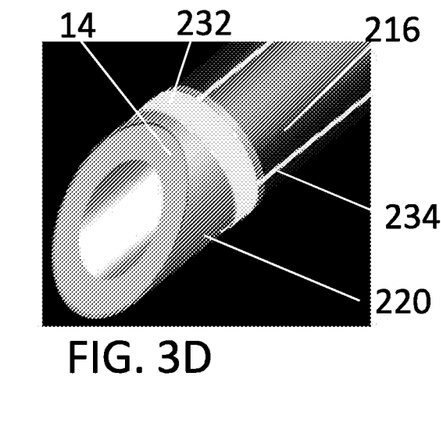
FIG. 3D is a perspective view showing the needle of FIG. 3C having a top electrode formed on the copolymer and a trace formed on the dielectric layer in accordance with the present principles.
Figure 3E:
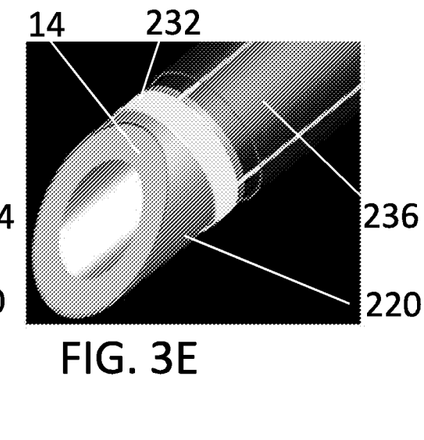
FIG. 3E is a perspective view showing the needle of FIG. 3D having another dielectric layer formed on the trace in accordance with the present principles.

Referring to FIGS. 3A-3F, in this embodiment, all leads to the sensor are both shielded and insulated from the environment. In FIG. 3A, a dielectric 216 is applied to the needle 14. The dielectric 216 may be about 25-50 microns thick, although other thicknesses may be employed. Then, a bottom electrode 222 is formed with a connecting trace 224 in FIG. 3B. In FIG. 3C, a copolymer 220 is only applied to the tip through dip coating. In FIG. 3D, a top electrode 232 and trace 234 are deposited. A dielectric layer 236 (e.g., 25-50 microns thick) is formed in FIG. 3E. A shield 238 and outer dielectric (not shown) are formed in FIG. 3F to form a sensor 250. As sensor leads 224, 234 are both separate from the shield there are more options available to provide signal amplification. A traditional driven shield amplifier may be employed, where one lead is the ground and the other lead the signal, and the shield is driven with a buffered version of the signal line.

Figure 3F:
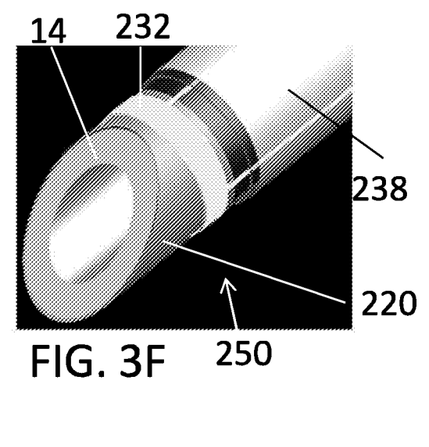
FIG. 3F is a perspective view showing the needle of FIG. 3E having a conductive shield formed thereon in accordance with the present principles.

If there is a need to operate in extremely noisy environments (e.g., RF-ablation, near pacemaker, etc.), this interconnect strategy can be extended further. The sensor 250 could be constructed with two layers and three leads from the bottom, middle and top electrodes. The middle electrode would form the ground and top and bottom electrodes would create signals of opposite polarity that could be fed into a differential amplifier. As the signal traces have opposite polarity signals, the traces each need their individual shield, thus the shield layers need to include two half cylinders that are electrically separated from each other, and two separate shield drivers need to be employed. It should be understood that a greater number of sensors may be employed, and a greater number of electrodes may be employed.

If cost is an issue and needs to be further reduced at the sacrifice of performance, other embodiments and manufacturing processes may be employed. FIGS. 4A to 4F show a low cost embodiment.

Figure 4A:
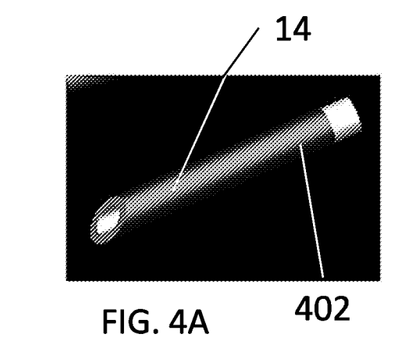
FIG. 4A is a perspective view showing a needle where a low profile conformal sensor will be formed, coated with a dielectric layer in accordance with another embodiment.
Figure 4B:
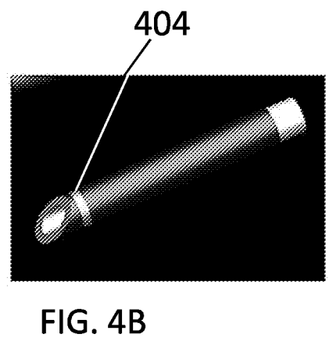
FIG. 4B is a perspective view showing the needle of FIG. 4A having a groove formed through the dielectric layer in accordance with the present principles.
Figure 4C:
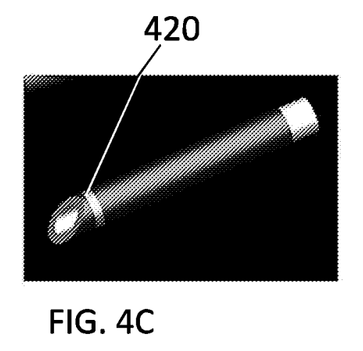
FIG. 4C is a perspective view showing the needle of FIG. 4B having a copolymer (piezoelectric polymer) formed in the groove in accordance with the present principles.

In FIG. 4A, the needle 14 is dip coated in an insulator 402. In FIG. 4B, a ring shaped strip 404 is removed from the insulator 402, this could be done by spinning the needle 14 and pushing in a narrow (e.g., 300 microns) cutting tool to make a groove in the insulation. In FIG. 4C, a copolymer 420 is applied in the strip or groove 404. This could be done with a miniature paintbrush or by dip coating the tip. Optionally, excess copolymer 420 on the insulator 402 can be removed by wiping it off as the groove depth is more than the copolymer thickness.

Figure 4D:
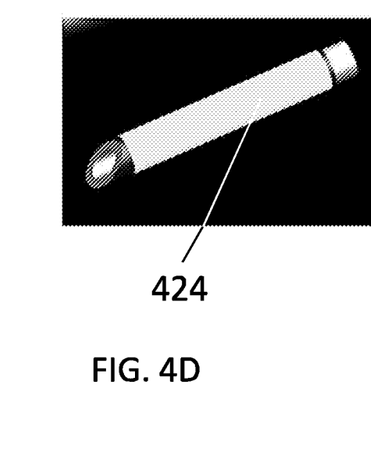
FIG. 4D is a perspective view showing the needle of FIG. 4C having an electrode/trace is formed on the dielectric layer in accordance with the present principles.
Figure 4E:
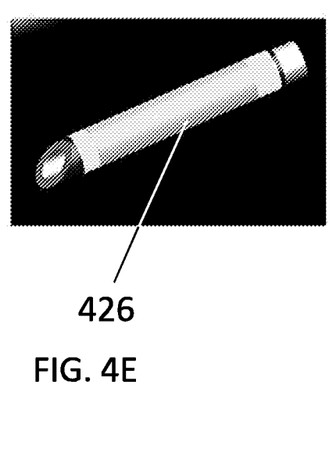
FIG. 4E is a perspective view showing the needle of FIG. 4D having another dielectric layer formed on the electrode/trace in accordance with the present principles.
Figure 4F:
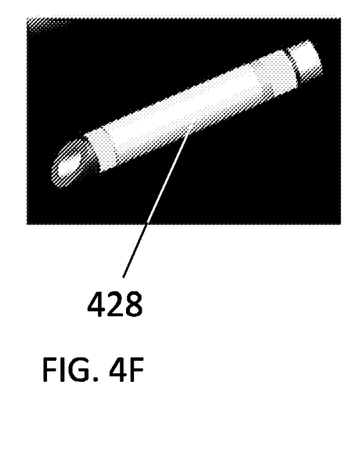
FIG. 4F is a perspective view showing the needle of FIG. 4E having a conductive shield formed thereon in accordance with the present principles.

In FIG. 4D, a signal trace 424 is applied by applying a conductive coating to a large region of the dielectric 402 and over the copolymer 420. This may include vapor deposition or application through dipping in conductive ink. In FIG. 4E, another insulating dielectric layer 426 is applied. In FIG. 4F, a conductive shielding layer 428 is applied. This method offers a simplified production process, but interconnect capacitance is higher and a good quality capacitance canceling amplifier (CCA) may be needed to obtain useful performance.

To reduce the cost for connection on a disposable needle or other device, a ring electrode structure can be employed. The structure is low cost and low profile such that it will not alter the budgetary constraints and not affect device performance. If additive manufacturing techniques such as conformal micro dispensing techniques, spray paint or inkjet printing are employed, it may be advantageous to deposit the materials for the interconnect stripline (traces) over a smaller section of the circumference. For example, if the dielectric is applied using a spray paint or airbrush technique, a wide spray pattern could be employed to deposit on multiple needles simultaneously and would naturally create a tapered coating spanning 180 degrees of the circumference. Alternatively a narrow spray pattern with an airbrush could produce a tapered dielectric layer over a much smaller circumferential area, for example 45 degrees. In other words, the ring structure would not encircle the entire needle or device and, instead, occupy a section on the circumference.

In one embodiment, e.g., FIGS. 1A-1F, a first dielectric spanning 45 degrees could be applied, then a narrow trace with, for example, a micro dispensing nozzle could be applied. Then, another dielectric spanning perhaps 30 degrees may be applied. Finally, a conductive outer shield, spanning perhaps 90 degrees, and occupying the edges for electrically contacting the needle may be applied. This would create a smoothly encapsulated stripline structure spanning 90 degrees of the circumference, providing excellent shielding while saving on material and deposition time.

Due to its small surface area, the sensor has very limited driving capability, and loading from interconnects and amplifier can drastically reduce its output signal. The sensor can be modeled as a voltage source in series with a small capacitor, and for a 0.3 mm ring on an 18 gauge needle, this capacitor has a value of about 2 pf. The interconnect has a much larger capacitance, for the n14 needle, the micro-coax from the tip to the hub has 7.5 pf, and the shortest (63 cm) coax cable for connecting to the amplifier adds 24.5 pf.

Figure 5A:
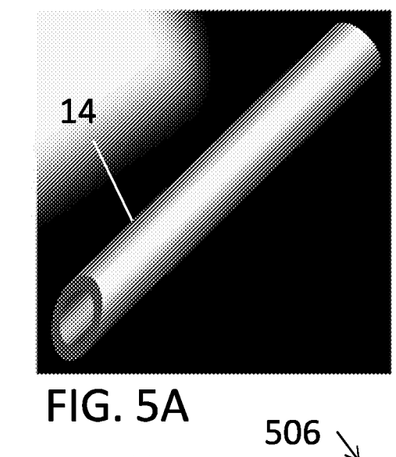
FIG. 5A is a perspective view showing a needle where a low profile conformal sensor will be formed in accordance with the present principles.
Figure 5B:
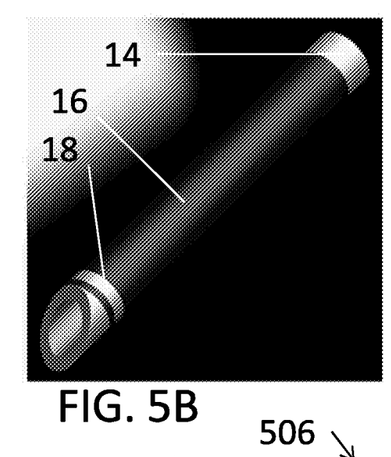
FIG. 5B is a perspective view showing the needle of FIG. 5A having a dielectric layer (insulator) formed thereon and including a ring through the dielectric layer in accordance with the present principles.
Figure 5C:
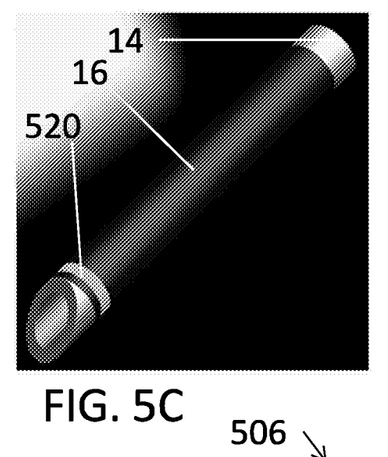
FIG. 5C is a perspective view showing the needle of FIG. 5B having a copolymer (piezoelectric polymer) formed in the groove in accordance with the present principles.
Figure 5D:
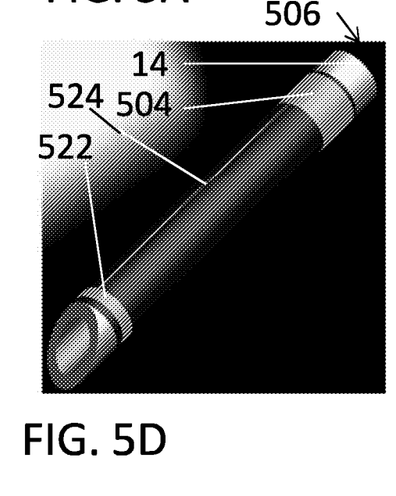
FIG. 5D is a perspective view showing the needle of FIG. 5C having a top electrode formed on the copolymer, a trace formed on the dielectric layer and a proximal hub ring connected to the top electrode by the trace in accordance with the present principles.
Figure 5E:
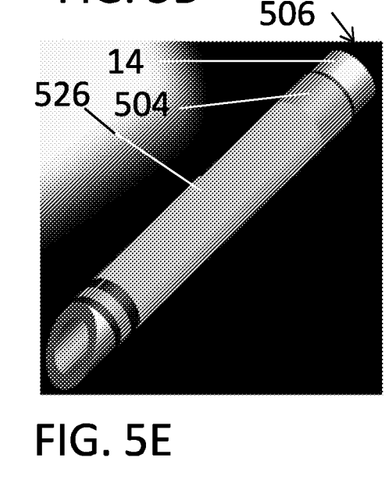
FIG. 5E is a perspective view showing the needle of FIG. 5D having another dielectric layer formed on the trace in accordance with the present principles.
Figure 5F:
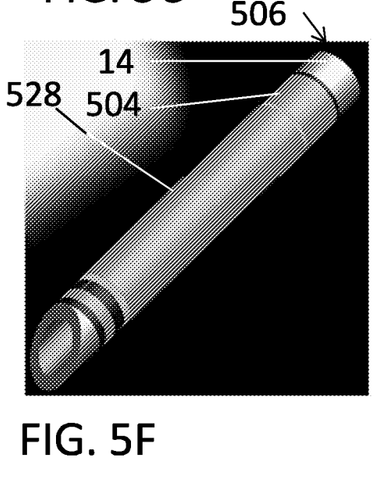
FIG. 5F is a perspective view showing the needle of FIG. 5E having a conductive shield formed thereon in accordance with the present principles.

Referring to FIGS. 5A-5F, in one embodiment, after an insulating material 16 is applied to needle 14 (FIG. 5A), it is stripped in section 18 (FIG. 5B). A piezoelectric (e.g., P(VDF-TrFE)) or similar material 520 (FIG. 5C) is applied directly onto the needle as a small ring (e.g., 300 micron wide). In FIG. 5D, a thin layer of conductive ink is used to apply a top electrode 522, a very thin conductive trace 524 along the needle 14, and a ring electrode (hub side contact) 504 at a hub end portion 506 of the needle 14 (note that the needle length is shortened in the FIGS. for illustrative purposes). Another insulating layer 526 is applied in FIG. 5E. In FIG. 5F, a conductive ink shield 528 is applied. Electrical signal is carried by the trace 524, which is kept as thin as possible to reduce parasitic capacitance. The needle 14 and outer shield 528 are electrically connected together to form a shield around the signal wire leading to an interconnect that is similar to a stripline configuration in high frequency printed circuit board (PCB) designs.

At the hub end portion 506, the bare needle surface 14, ring electrode 504, and outer shield 528, form three circular contact pads that a small connector can clamp onto. This design minimizes connector cost on the disposable needle and puts the more costly part of the connection on a reusable clamp (not shown) that would connect to the needle 14 and other contacts (504, 528). This embodiment can be implemented using additive manufacturing technologies such as, for example, conformal micro dispensing systems or inkjet deposition techniques.

To keep the product cost down, the materials used need to be low cost, and the manufacturing process should be highly automated with large volume to avoid labor and equipment costs. Given these goals, piezoelectrical polymers such as PVDF and P(VDF-TrFE) are candidate materials for sensor production. The ability of an applied voltage to produce motion in a PVDF sample is used to produce ultrasonic waves, which can be detected using a PVDF based hydrophone. There are a wide variety of considerations in deciding whether to use a ceramic based piezoelectric or PVDF in a given medical application. At lower frequencies, thicker PVDF membranes should be employed for resonance considerations. A PVDF sensor can be modeled as a voltage source in series with a capacitance, and for thicker sensors with small surface area, this may result in a small capacitance. Hence, in general, it appears that PVDF has advantages for medical ultrasonic work carried out in the frequency range 25-100 MHz. PVDF is also limited in ability to transmit higher intensities of ultrasound compared to PZT.

PVDF has favorable behavior even at the lower frequencies, for example, for PVDF hydrophones for detecting ultrasonic waves. Compared to PZT, which may also be employed in some embodiments, PVDF has a much higher bandwidth and will thus not distort the transient behavior of the wave as much. The low output capacitance problem can in this case be handled by integrating a high input impedance field effect transistor (FET) based preamplifier in very close proximity to the sensor (10, FIG. 1F). The d33 constant, strain in thickness direction developed for an applied voltage, is about an order of magnitude higher for piezo-ceramics than for piezo-polymers. One disadvantage of piezo-ceramic is its high acoustic impedance, about 30 MRayls (1 MRayl=106 kg/m$^2$s) in contrast to about 1.5 MRayls for body tissue. This impedance mismatch can be compensated by quarter wavelength matching layers, but these can degrade the ultrasonic pulse due to adhesive layers and construction methods. The acoustic impedance of a piezo film is about 4 MRayls, a much better match. Additionally, ceramics are fragile, and cannot be shaped to desired geometries. PVDF is a conformable and flexible low cost material with acoustic impedance close to tissue that unlike PZT will not need matching layers.

PVDF piezoelectric films are produced in a clean room environment, and start with a melt extrusion of PVDF resin pellets into sheet form. Next, there is a stretching step that reduces the sheet thickness by about a factor of 5. This stretching, well below the melting point of the polymer, causes chain packing of the molecules into parallel crystal planes, called the "beta phase". To obtain high levels of piezoelectric activity, the beta phase polymer is then exposed to very high electric fields to align the crystallites relative to a poling field. In the stretching step, the film can be stretched along only one dimension (uni-axial film) or in both dimensions (bi-axial film). Bi-axial films will have their piezoelectric sensitivity primarily only in the thickness direction, while the uni-axial film will be sensitive to strain in both the thickness direction and the non-stretched planar direction.

New copolymers of PVDF have been developed that allow for use at higher temperatures (e.g., as high as 135 degrees Celsius for some copolymers, versus 100 degrees Celsius for conventional PVDF). Although these temperatures are not encountered in clinical use, a higher temperature tolerance can be an advantage in simplifying the manufacturing and sterilization process. Copolymers of PVDF are polarizable without stretching, and very thin films down to 200 Angstroms can be produced using spincast coating techniques, such thin layers are not feasible with standard PVDF. In addition, the copolymer has a slightly higher thickness mode piezoelectric constant, leading to about 10% higher sensitivity compared to conventional PVDF.

Figure 6:
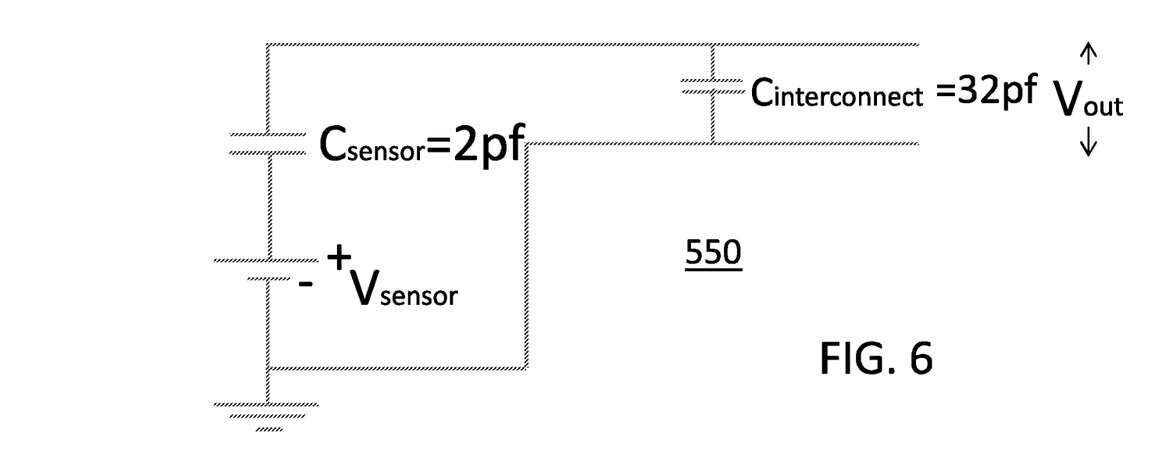
FIG. 6 is a schematic diagram illustrating a voltage divider circuit with a capacitive relationship for a sensor in accordance with the present principles.

Referring to FIG. 6, an equivalent circuit 550 is shown where a sensor capacitance (Csensor) and interconnect capacitance (Cinterconnect) form a voltage divider circuit. The output voltage (Vout) is Vsensor*(Csensor/(Csensor+Cinterconnect)), a reduction of ⅔₄, leading to a 24.6 dB loss of signal. Clearly, parasitic cable capacitance has significant impact on performance. A sufficiently high input resistance of the amplifier is also important as a resistive load on the sensor will create a high pass filter, in this example, a 30 kOhm amplifier resistance would lead to a −3 dB cutoff frequency of about 2.5 MHz. While FIG. 6 shows exemplary values for electrical parameters, other parameter's values are also contemplated and may be adjusted with circuit design characteristics and components.

There are some electronic strategies to lessen the effect of parasitic capacitance on performance. One such technique is called "driven shield". A key element in this method is to reduce parasitic current flow from the wire carrying the signal of interest by minimizing the electric field surrounding it. This employs a total of three conductors in the interconnect, a ground connection, a signal wire, and a shield surrounding the signal wire. The voltage on the signal wire is measured, and the shield is driven with an exact replica of that voltage. Even though the signal wire has a parasitic capacitance to the shield, there is no parasitic current flowing as there are no voltage changes over the parasitic capacitance. The ground wire is held at a steady voltage by the amplifier power supply and not driven by the sensor, thus its parasitic capacitance to other structures has no detrimental influence. Another technique includes using a capacitance canceling amplifier (CCA).

Figure 7:
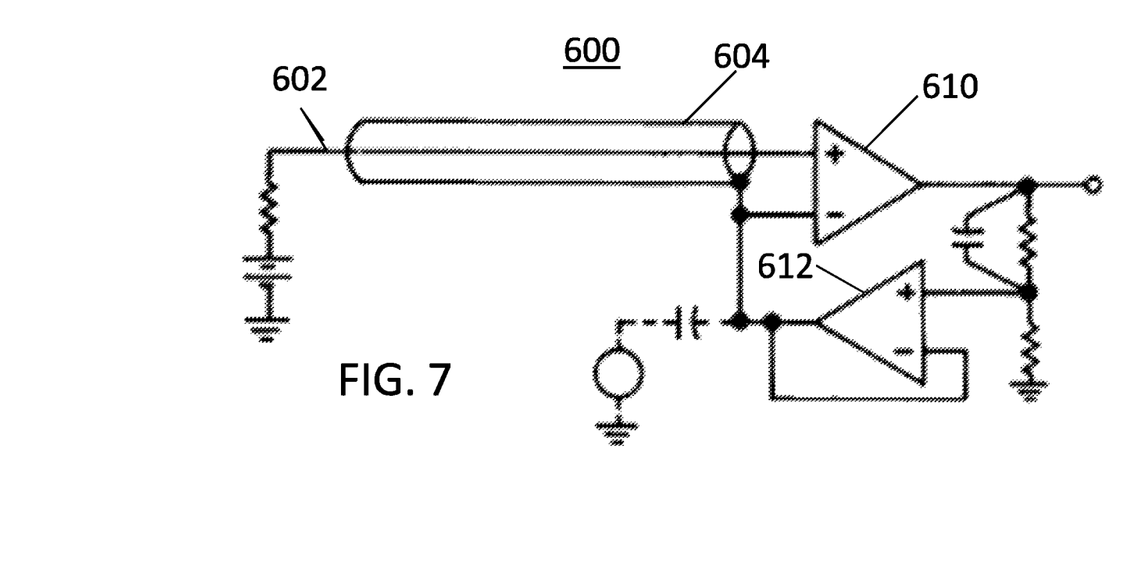
FIG. 7 is a schematic diagram illustrating a driven shield amplifier circuit in accordance with the present principles.

Referring to FIG. 7, an amplifier 600 employs a CCA method, which only needs two conductors (signal 602 and shield 604) and operates by keeping a voltage between the conductors 602, 604 at a constant and low value. The signal input may employ a junction field effect transistor (JFET) input transistor (not shown) to achieve a very high input impedance, therefore the current produced by an acoustic wave hitting the sensor cannot dissipate and creates a voltage change. This changing voltage is amplified by two identical buffer circuits 610, 612, one amplifier 610 to create an output signal, the other amplifier 612 to drive the shield 604 such that the voltage change between the conductors 602, 604 is minimized. The present principles have been described in terms of a needle, and more particularly to a biopsy needle. However, the present principles may be applied to any instrument where a piezoelectric sensor (receiver), transmitter or transducer is needed. Such devices may include catheters, guidewires, endoscopes, implantable devices, etc. The present principles can provide a relatively low cost device with a built-in for sensor conformally applied to an exterior surface. To keep the product cost down, the materials used need to be low cost, and the manufacturing process should be highly automated with large volume to avoid labor and equipment cost. The devices in accordance with the present principles provide a low form factor that is conformally formed and placed on a medical device or instrument. In particularly useful embodiments, the present principles are employed for ultrasound guided needle interventions, e.g., RF ablation, liver biopsy, nerve blocks, vascular access, abscess drainage, etc. It should be understood that the sensors are preferably integrally formed with the needle (or device) and as such the needle and the sensors are a disposable item.

Figure 8:
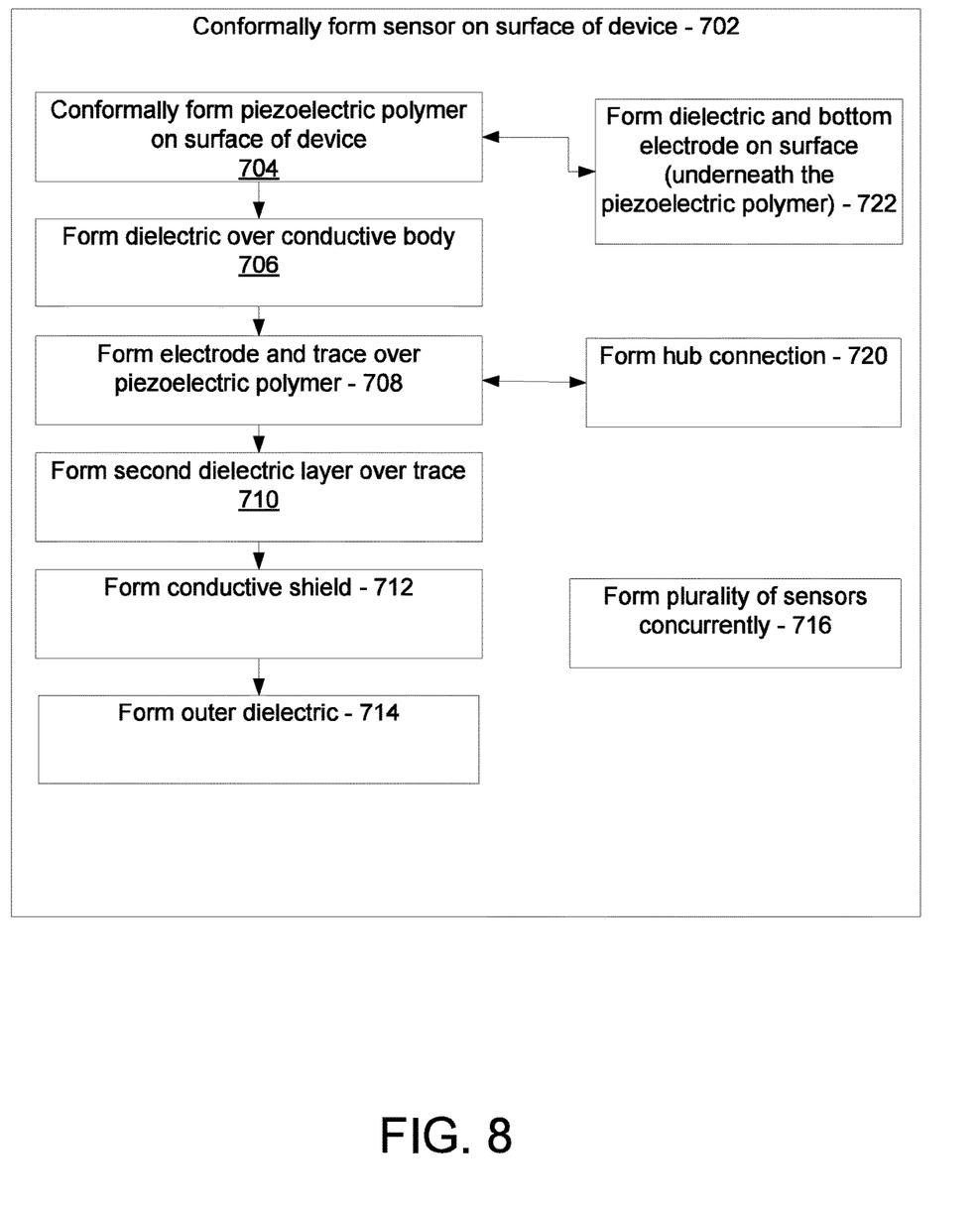
FIG. 8 is a flow diagram showing a method for fabricating a medical device having a conformal sensor in accordance with illustrative embodiments.

Referring to FIG. 8, a method for fabricating a medical device is illustratively shown. In block 702, a sensor is conformally formed on a surface of a conductive body. Conformally forming a sensor may include conformally forming the sensor about at least a portion of a circumference of the device. The sensor may be formed over a portion of the circumference or over the entire circumference. The sensor may be formed in an arcuate or planar arrangement or having any suitable shape.

In block 704, a piezoelectric polymer is applied about a portion of the surface and follows a contour of the surface. The piezoelectric polymer may include polyvinylidene fluoride (PVDF) or polyvinylidene fluoride trifluoroethylene P(VDF-TrFE). The piezoelectric polymer may be applied by painting, spraying, dipping, deposition, etc.

In block 706, a first dielectric layer is formed over the conductive body adjacent to the piezoelectric polymer and extends proximally to the piezoelectric polymer. In block 708, an electrode is formed over the piezoelectric polymer including a trace connecting to the electrode and extending along the first dielectric layer proximally to the electrode. In block 710, a second dielectric layer is formed adjacent to the electrode over the trace and extends proximally to the electrode. In block 712, a conductive shield is formed over the second dielectric layer. In block 714, an outer dielectric layer is formed over the conductive shield and the electrode.

In block 716, a plurality of conformally formed sensors may be formed concurrently on the surface adjacent to one another.

In block 720, a hub connection may be formed with an electrode (which may be formed with the electrode formed over the piezoelectric polymer and the trace). The hub connection is located proximally on the device and can be employed to connect electronics, amplifiers or other components to the sensor.

In block 722, in one alternative embodiment, a dielectric is provided on the surface of the conductive body followed by the formation of a bottom electrode with a corresponding trace. These structures may be formed prior to the piezoelectric polymer. In this way, the conductive body need not be employed as an electrode. In addition, the conductive body need not be conductive for this arrangement. The electrodes and piezoelectric polymer, in this case, would be electrically isolated from the surface.

In interpreting the appended claims, it should be understood that:
  a) the word "comprising" does not exclude the presence of other elements or acts than those listed in a given claim;
  b) the word "a" or "an" preceding an element does not exclude the presence of a plurality of such elements;
  c) any reference signs in the claims do not limit their scope;
  d) several "means" may be represented by the same item or hardware or software implemented structure or function; and
  e) no specific sequence of acts is intended to be required unless specifically indicated.

Having described preferred embodiments for needles with piezoelectric polymer sensors (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical device, comprising:
an inner most body having a surface, wherein the inner most body is conductive and the surface serves as a first electrode;
a sensor conformally formed on the surface and including a piezoelectric polymer directly formed about a portion of the surface of the inner most body of the medical device and following a contour of the surface, the piezoelectric polymer configured to generate or receive ultrasonic energy; and
electrical connections conforming to the surface and being connected to a second electrode in contact with the piezoelectric polymer, the electrical connections providing connections to the piezoelectric polymer and being electrically isolated from the inner most body over at least a portion of the surface.

2. The medical device as recited in claim 1, wherein the piezoelectric polymer includes one of polyvinylidene fluoride (PVDF) or polyvinylidene fluoride trifluoroethylene P(VDF-TrFE).

3. The medical device as recited in claim 1, wherein the sensor is conformally formed about at least a portion of a circumference of the device.

4. The medical device as recited in claim 1, further comprising a conductive shield formed conformally over the electrical connections on a dielectric material.

5. The medical device as recited in claim 4, wherein the conductive shield and the electrical connections provide a driven shield configuration to reduce capacitance.

6. The medical device as recited in claim 4, wherein the conductive shield and the electrical connections connect to a capacitive cancellation amplifier circuit to reduce capacitance.

7. The medical device as recited in claim 1, further comprising a plurality of sensors conformally formed on the surface adjacent to one another.

8. A medical device, comprising:
an inner most body having a surface serving as a first electrode, wherein the inner most body is conductive;
a sensor conformally formed on the surface, including:
a piezoelectric polymer directly formed about a portion of the surface of the inner most body of the medical device and following a contour of the surface; and
a second electrode formed over the piezoelectric polymer and including a trace connecting to the second electrode and extending along the inner most body proximally to the second electrode;
a first dielectric layer formed over the inner most body adjacent to the piezoelectric polymer and extending proximally to the piezoelectric polymer;
a second dielectric layer formed adjacent to the second electrode over the trace and extending proximally to the second electrode; and
a conductive shield formed over the second dielectric layer.

9. The medical device as recited in claim 8, wherein the piezoelectric polymer includes one of polyvinylidene fluoride (PVDF) or polyvinylidene fluoride trifluoroethylene P(VDF-TrFE).

10. The medical device as recited in claim 8, wherein the sensor is conformally formed about at least a portion of a circumference of the body.

11. The medical device as recited in claim 8, wherein the conductive shield and the trace provide a driven shield configuration to reduce capacitance.

12. The medical device as recited in claim 8, wherein the conductive shield and the trace connect to a capacitive cancellation amplifier circuit to reduce capacitance.

13. The medical device as recited in claim 8, further comprising a plurality of sensors conformally formed on the surface adjacent to one another.

14. The medical device as recited in claim 8, further comprising a third electrode formed underneath the piezoelectric polymer and connected by a second trace, the third electrode being electrically isolated from the surface.

15. A method for fabricating a medical device, comprising act of:
conformally forming a sensor on an inner most body of the medical device, the inner most body being conductive and having surface serving as a first electrode by performing acts of:
applying a piezoelectric polymer directly about a portion of the surface that follows a contour of the surface;
forming a first dielectric layer over the inner most body adjacent to the piezoelectric polymer and extending proximally to the piezoelectric polymer;
forming a second electrode over the piezoelectric polymer including a trace connecting to the second electrode and extending along the first dielectric layer proximally to the second electrode;
forming a second dielectric layer adjacent to the second electrode over the trace and extending proximally to the second electrode;
forming a conductive shield formed over the second dielectric layer; and
forming an outer dielectric layer over the conductive shield and the second electrode.

16. The method as recited in claim 15, wherein the applying act includes an act of applying one of polyvinylidene fluoride (PVDF) or polyvinylidene fluoride trifluoroethylene P(VDF-TrFE) by at least one of painting, dipping or deposition.

17. The method as recited in claim 15, wherein the conformally forming act includes an act of conformally forming the sensor about at least a portion of a circumference of the body.

18. The method as recited in claim 15, further comprising an act of forming a plurality of conformally formed sensors on the surface adjacent to one another.

19. The method as recited in claim 15, further comprising an act of forming a third dielectric and a third electrode with a second trace prior to applying the piezoelectric polymer, the third electrode being electrically isolated from the surface.

20. The medical device of claim 1, further comprising a dielectric layer formed directly on the surface adjacent to the piezoelectric polymer, wherein the dielectric layer overlaps the piezoelectric polymer to prevent exposure of the surface.

* * * * *